US006998418B1

(12) United States Patent
Sung et al.

(10) Patent No.: US 6,998,418 B1
(45) Date of Patent: *Feb. 14, 2006

(54) ACELLULAR BIOLOGICAL MATERIAL CHEMICALLY TREATED WITH GENIPIN

(75) Inventors: Hsing-Wen Sung, Hsinchu (TW); Huang-Chien Liang, Hsinchu (TW); Hosheng Tu, Newport Beach, CA (US)

(73) Assignee: GP Medical, Inc., Newport Beach, CA (US)

(*) Notice: Subject to any disclaimer, the term of this patent is extended or adjusted under 35 U.S.C. 154(b) by 288 days.

This patent is subject to a terminal disclaimer.

(21) Appl. No.: 10/408,176

(22) Filed: Apr. 7, 2003

Related U.S. Application Data

(63) Continuation-in-part of application No. 10/067,130, filed on Feb. 4, 2002, now Pat. No. 6,545,042, which is a continuation-in-part of application No. 09/297,808, filed on Sep. 27, 2001, now Pat. No. 6,608,040.

(60) Provisional application No. 60/030,701, filed on Nov. 5, 1996.

(51) Int. Cl.
*A61K 31/35* (2006.01)
*A61F 2/08* (2006.01)

(52) U.S. Cl. .................. 514/456; 514/540; 424/422; 623/11; 623/13; 623/23; 435/325

(58) Field of Classification Search .............. 424/422; 514/456, 540; 623/13, 11, 23, 13.11
See application file for complete search history.

(56) References Cited

U.S. PATENT DOCUMENTS

| | | | |
|---|---|---|---|
| 4,082,507 | A | 4/1978 | Sawyer |
| 4,806,595 | A | 2/1989 | Noishiki et al. |
| 5,194,596 | A | 3/1993 | Tischer et al. |
| 5,281,422 | A | 1/1994 | Badylak et al. |
| 5,372,821 | A | 12/1994 | Badylak et al. |
| 5,445,833 | A | 8/1995 | Badylak et al. |
| 5,573,784 | A | 11/1996 | Badylak et al. |
| 5,599,558 | A | 2/1997 | Gordinier et al. |
| 5,800,537 | A | 9/1998 | Bell |
| 5,893,888 | A | 4/1999 | Bell |
| 5,929,038 | A | 7/1999 | Chang |
| 6,051,750 | A | 4/2000 | Bell |
| 6,103,255 | A | 8/2000 | Levene et al. |
| 6,162,826 | A | 12/2000 | Moon et al. |
| 6,206,931 | B1 | 3/2001 | Cook et al. |
| 6,261,565 | B1 | 7/2001 | Empie et al. |
| 6,262,083 | B1 | 7/2001 | Moon et al. |
| 6,264,992 | B1 | 7/2001 | Voytik-Harbin et al. |
| 6,340,480 | B1 | 1/2002 | Duckett et al. |
| 6,485,723 | B1 | 11/2002 | Badylak et al. |
| 6,506,398 | B1 | 1/2003 | Tu et al. |

FOREIGN PATENT DOCUMENTS

WO    WO 98/19718    5/1998

OTHER PUBLICATIONS

Courtmen et al, J. Biomedical Materials Research, 1994, 28, 655-666.*
Malone et al, J. Vasc. Surg, 1984, 1, 181-191.*
Sung HW et al., "In Vitro Evaluation of Cytotoxicity of a Naturally Occuring Crosslinking Reagent for Biological Tissue Fixation", J Biomater Sci Polymer Edn 1999;10: 63-78.
Sung HW et al., "Mechanical Properties of a Porcine Aortic Valve Fixed With a Naturally Occurring Crosslinking Agent" Biomaterials 1999; 20: 1759-72.
Tsai CC et al., "In Vitro Evaluation of the Genotoxicity of a Naturally Occurring Crosslinking Agent (Genipin) for Biological Tissue Fixation" J Biomed Mater Res 2000; 52: 58-65.
Sung HW et al., "Fixation of Biological Tissues With a Naturally Occurring Crosslinking Agent Fixation Rate and Effects of pH, Temperature, and Initial Fixative Concentration" J Biomed Mater Res 2000; 52: 77-87.
Sung HW et al., "Feasibility Study of a Natural Crosslinking Reagent for Biological Tissue Fixation" J Biomed Mater Res 1998; 42: 560-567.
Huang LH et al., "Biocompatibility Study of a Biological Tissue Fixed With a Naturally Occurring Crosslinking Reagent" J Biomed Mater Res 1998; 42: 568-576.
Sung HW et al., "In Vitro Surface Characterization of a Biological Patch Fixed With a Naturally Occurring Crosslinking Agent" Biomaterials 2000; 21: 1353-1362.
Sung HW et al.; "Crosslinking Characteristics and Mechanical Properties of a Bovine Pericardium Fixed With a Naturally Occurring Crosslinking Agent" J Biomed Mater Res 1999; 47: 116-126.
Chang Y et al., "Reconstruction of the Right Ventricular Outflow Tract With a Bovine Jugular Vein Graft Fixed With a Naturally Occurring Crosslinking Agent (Genipin) in a Canine Model" J Thorac Cardiovasc Surg 2001; 122: 1208-18.
Sung HW et al., "Extraction of a Naturally Occurring Crosslinking Agent (Genipin) from Gardenia Fruits and its Applications in Biological Tissue Fixation" Biomaterials and Drug Delivery Toward New Millenium (Ed. KD Park et al.) Han Rin Wen Publishing pp. 623-632 (2000).

(Continued)

*Primary Examiner*—James O. Wilson
*Assistant Examiner*—Ganapathy Krishnan

(57) ABSTRACT

A method for promoting autogenous ingrowth of damaged or diseased tissue selected from a group consisting of ligaments, tendons, muscle and cartilage, the method comprising a step of surgically repairing the damaged or diseased tissue by attachment of a tissue graft, wherein the tissue graft is formed from a segment of connective tissue protein after an acellularization process, the segment being crosslinked with genipin, its analog or derivatives. The genipin-fixed acellular tissue provides a microenvironment for tissue regeneration adapted for use as a biological implant device due to its low cytotoxicity.

18 Claims, 13 Drawing Sheets

OTHER PUBLICATIONS

Tsai CC et al., "Effects of Heparin Immobilization on the Surface Characteristics of a Biological Tissue Fixed With a Naturally Occurring Crosslinking Agent (Genipin)—an In Vitro Study" Biomaterials 2001; 23: 523-533.

Courtman DW et al., "Development of a Pericardial Acellular Matrix Biomaterial. Biochemical and Mechanical Effects of Cell Extraction" J Biomed Mater Res 1994; 23: 655-666.

Wilson GJ et al., "Acellular Matrix Allograft Small Caliber Vascular Prostheses" Trans Am Soc Artif Intern Organs 1990; 36: 340-343.

Malone JM et al., "Detergent-Extracted Small-Diameter Vascular Prostheses" J Vasc Surg 1984; 1: 181-191.

* cited by examiner (b) Specimen-B (d) Specimen-D (a) Specimen-A (c) Specimen-C (a) Specimen-A
 (b) Specimen-B
 (c) Specimen-C
 (d) Specimen-D (b) Specimen-B/GP (d) Specimen-D/GP (a) Specimen-A/GP (c) Specimen-C/GP

ACELLULAR BIOLOGICAL MATERIAL CHEMICALLY TREATED WITH GENIPIN

CROSS-REFERENCE TO RELATED APPLICATIONS

This is a continuation-in-part application of Ser. No. 10/067,130 filed Feb. 4, 2002, entitled "Acellular biological material chemically treated with genipin", now U.S. Pat. No. 6,545,042, which is a continuation-in-part application of Ser. No. 09/297,808 filed Sep. 27, 2001, now U.S. Pat. No. 6,608,040 entitled "Chemical modification of biomedical materials with genipin", which claims priority of PCT/US97/20113 filed Nov. 4, 1997, which claims the benefits of a provisional application Ser. No. 60/030,701 filed Nov. 5, 1996.

FIELD OF THE INVENTION

The present invention generally relates to chemical modification of biomedical materials, such as collagen matrix with a naturally occurring crosslinking reagent, genipin. More particularly, the present invention relates to tissue grafts constructed of acellular biological material with the crosslinking reagent, genipin, its derivatives or analog and the process thereof.

BACKGROUND OF THE INVENTION

Crosslinking of biological molecules is often desired for optimum effectiveness in biomedical applications. For example, collagen, which constitutes the structural framework of biological tissue, has been extensively used for manufacturing bioprostheses and other implanted structures, such as vascular grafts, wherein it provides a good medium for cell infiltration and proliferation. However, biomaterials derived from collagenous tissue must be chemically modified and subsequently sterilized before they can be implanted in humans. The fixation, or crosslinking, of collagenous tissue increases strength and reduces antigenicity and immunogenicity.

Collagen sheets are also used as wound dressings, providing the advantages of high permeability to water vapor and rapid wound healing. Disadvantages include low tensile strength and easy degradation of collagen by collagenase. Crosslinking of collagen sheets reduces cleavage by collagenase and improves tensile strength.

Clinically, biological tissue has been used in manufacturing heart valve prostheses, small-diameter vascular grafts, and biological patches, among others. However, the biological tissue has to be fixed with a crosslinking or chemically modifying agent and subsequently sterilized before they can be implanted in humans. The fixation of biological tissue is to reduce antigenicity and immunogenicity and prevent enzymatic degradation. Various crosslinking agents have been used in fixing biological tissue. These crosslinking agents are mostly synthetic chemicals such as formaldehyde, glutaraldehyde, dialdehyde starch, glyceraldehydes, cyanamide, diimides, diisocyanates, and epoxy compound. However, these chemicals are all highly cytotoxic which may impair the biocompatibility of biological tissue. Of these, glutaraldehyde is known to have allergenic properties, causing occupational dermatitis and is cytotoxic at concentrations greater than 10–25 ppm and as low as 3 ppm in tissue culture. It is therefore desirable to provide a crosslinking agent suitable for use in biomedical applications that is within acceptable cytotoxicity and that forms stable and biocompatible crosslinked products.

To achieve this goal, a naturally occurring crosslinking agent (genipin) has been used to fix biological tissue. The co-pending application Ser. No. 09/297,808 filed Sep. 27, 2001, entitled "Chemical modification of biomedical materials with genipin" is incorporated and cited herein by reference. The cytotoxicity of genipin was previously studied in vitro using 3T3 fibroblasts, indicating that genipin is substantially less cytotoxic than glutaraldehyde (Sung H W et al., J Biomater Sci Polymer Edn 1999; 10:63–78). Additionally, the genotoxicity of genipin was tested in vitro using Chinese hamster ovary (CHO-K1) cells, suggesting that genipin does not cause clastogenic response in CHO-K1 cells (Tsai C C et al., J Biomed Mater Res 2000; 52:58–65). A biological material treated with genipin resulting in acceptable cytotoxicity is key to biomedical applications.

It is further hypothesized in the literature that acellular tissue might remove cellular antigens (Wilson G J et al., Trans Am Soc Artif Intern 1990; 36:340–343). As a means for reducing the antigenic response to xenograft material, cell extraction removes lipid membranes and membrane-associated antigens as well as soluble proteins. Courtman et al. developed a cell extraction process to render bovine pericardium free of cells and soluble proteins, leaving a framework of largely insoluble collagen and elastin (Courtman D W et al., J Biomed Mater Res 1994; 28:655–666). They hypothesized that this process may decrease the antigenic load within the material, reducing the associated degradation due to in vivo cellular attack, and possibly eliminating the need for extensive crosslinking. Additionally, acellular tissue may provide a natural microenvironment for host cell migration to accelerate tissue regeneration (Malone J M et al., J Vasc Surg 1984; 1:181–91).

Other than maintaining a natural microenvironment, the collagen matrix, including soluble collagen, after being treated with the proposed cell extraction process, the collagen matrix shall have similar properties of decreased antigenicity/immunogenicity. However, the framework of largely insoluble collagen and elastin matrix is still vulnerable to enzymatic degradation and is not suitable as an implantable bioprosthesis.

As is well known that the human knee comprises an articulation of the femur, the tibia and the patella. The femur and the tibia are maintained in a condition of stable articulation by a number of ligaments of which the principal ones are the anterior and posterior cruciate ligaments and the collateral ligaments. The rupture of the anterior cruciate ligament is relatively commonly encountered as a result of sporting injury or the like. This rupture leads to knee instability and can be a debilitating injury. Though less common, the rupture of the posterior cruciate ligament can be equally disabling.

In the past, polymer or plastic materials have been studied as ligament or tendon replacements. Prosthetic ligament replacements made of carbon fibers and Gore-Tex PTFE materials do not last a long period of time. Repeated loading of a prosthetic ligament in a young active patient leads to failure of the ligament. It has been found that it is difficult to provide a tough durable plastic material which is suitable for long-term connective tissue replacement. Plastic material could become infected and difficulties in treating such infections often lead to graft failure.

In accordance with the present invention, there is provided genipin treated tissue grafts for orthopedic and other surgical applications, such as vascular grafts and heart valve bioprostheses, which have shown to exhibit many of the desired characteristics important for optimal graft function. In particular, the tissue regeneration capability in the genipin-fixed acellular tissue may be suitable as a graft material for bone, tendon, ligament, cartilage, muscle, and cardiovascular applications.

In some aspects of the invention, it is provided a method for promoting autogenous ingrowth of a biological tissue material, comprising providing a natural tissue, removing cellular material from the natural tissue, increasing porosity of the natural tissue by at least 5%, loading an angiogenesis agent or autologous cells into the porosity, and crosslinking the natural tissue with a crosslinking agent.

SUMMARY OF THE INVENTION

In general, it is an object of the present invention to provide a biological scaffold configured and adapted for tissue regeneration or tissue engineering. In one embodiment, the process of preparing a biological scaffold comprises steps of removing cellular material from a natural tissue and crosslinking the natural tissue with genipin, wherein the scaffold is characterized by reduced antigenicity, reduced immunogenicity and reduced enzymatic degradation upon placement inside a patient's body. The "tissue engineering" in this invention may include cell seeding, cell ingrowth and cell proliferation into the scaffold or collagen matrix in vivo or in vitro.

It is another object of the present invention to provide a tendon or ligament graft for use as connective tissue substitute, wherein the graft is formed from a segment of connective tissue protein, and the segment is crosslinked with genipin, its analog or derivatives resulting in acceptable cytotoxicity and reduced enzymatic degradation.

It is a further object of the present invention to provide a method for promoting autogenous ingrowth of damaged or diseased tissue selected from a group consisting of bone, ligaments, tendons, muscle and cartilage, the method comprising a step of surgically repairing the damaged or diseased tissue by attachment of a tissue graft, wherein the graft is formed from a segment of connective tissue protein, the segment being crosslinked with genipin, its analog or derivatives with acceptable cytotoxicity and reduced enzymatic degradation.

In some aspects, there is provided a biological tissue material configured and adapted for tissue regeneration comprising steps of removing cellular material from a natural tissue and crosslinking the natural tissue with a crosslinking agent, the tissue material being characterized by reduced antigenicity, reduced immunogenicity and reduced enzymatic degradation upon placement inside a patient's body, wherein porosity of the natural tissue is increased by at least 5%, the increase of porosity being adapted for promoting tissue regeneration. In a preferred embodiment, the tissue material is selected from a group consisting of a tissue valve, a tissue valve leaflet, a vascular graft, a ureter, a urinary bladder, a dermal graft, and the like. In another preferred embodiment, the natural tissue is selected from a group consisting of a porcine valve, a bovine jugular vein, a bovine pericardium, an equine pericardium, a porcine pericardium, submucosal tissue, and the like.

In some aspects, there is provided a method for promoting autogenous ingrowth of a biological tissue material comprising the steps of providing a natural tissue, removing cellular material from the natural tissue, increasing porosity of the natural tissue by at least 5%, and crosslinking the natural tissue with a crosslinking agent. The tissue material is generally characterized by reduced antigenicity, reduced immunogenicity and reduced enzymatic degradation upon placement inside a patient's body.

In some aspects, there is provided a method for promoting autogenous ingrowth of a biological tissue material comprising the steps of providing a natural tissue, removing cellular material from the natural tissue, increasing porosity of the natural tissue by at least 5%, loading an angiogenesis agent or autologous cells into the porosity, and crosslinking the natural tissue with a crosslinking agent. In one preferred embodiment, the angiogenesis agent is ginsenoside RG-1 or selected from the group consisting of VEGF, VEGF 2, bFGF, VEGF121, VEGF165, VEGF189, VEGF206, PDGF, PDAF, TGF-$\beta$, PDEGF, PDWHF, polyepoxy compounds, and combination thereof.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

The following detailed description is of the best presently contemplated modes of carrying out the invention. This description is not to be taken in a limiting sense, but is made merely for the purpose of illustrating general principles of embodiments of the invention.

Figure 1:
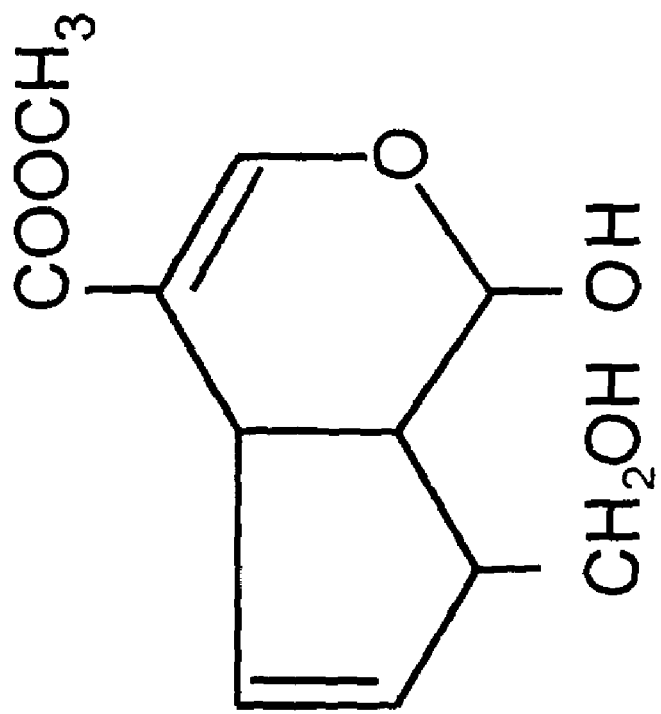
FIG. 1 is chemical structures of glutaraldehyde and genipin that are used in the chemical treatment examples of the current disclosure.
Figure 1:
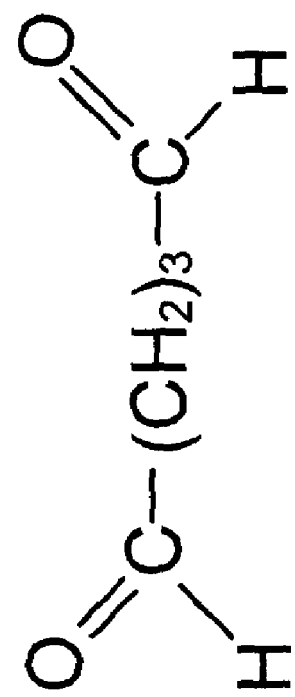

"Genipin" in this invention is meant to refer to the naturally occurring compound as shown in FIG. 1 and its derivatives, analog, stereoisomers and mixtures thereof.

"Tissue engineering" or "tissue regeneration" in meant to refer to cell seeding, cell ingrowth and cell proliferation into the acellular scaffold or collagen matrix in vivo or in vitro, sometimes enhanced with an angiogenesis factor.

A "biological tissue material" refers to a biomedical material or device which is inserted into, or grafted onto, bodily tissue to remain for a period of time, such as an extended-release drug delivery device, tissue valve, tissue valve leaflet, vascular or dermal graft, ureter, urinary bladder, or orthopedic prosthesis, such as bone, ligament, tendon, cartilage, and muscle.

A "scaffold" in this invention is meant to refer to a tissue matrix substantially or completely devoid of cellular materials. A scaffold may further comprise added structure porosity for cell ingrowth or proliferation.

An "acellularization process" is meant to indicate the process for removing at least a portion of cells from cellular tissue and/or tissue matrix containing connective tissue protein.

It is one object of the present invention to provide an acellular biological scaffold chemically treated with a naturally occurring crosslinking agent, genipin, that is configured and adapted for tissue regeneration, and/or tissue engineering in biomedical applications. In a region with suitable substrate diffusivity, an acellular biological tissue material with added porosity and chemically treated by a crosslinking agent enables tissue regeneration, and/or tissue engineering in many biomedical applications.

Previously, Chang in U.S. Pat. No. 5,929,038 discloses a method for treating hepatitis B viral infection with an iridoid compound of a general formula containing a six-member hydrocarbon ring sharing with one common bondage of a five-member hydrocarbon ring. Further, Moon et al. in U.S. Pat. No. 6,162,826 and No. 6,262,083 discloses genipin derivatives having anti hepatitis B virus activity and liver protection activity. All of which three aforementioned patents are incorporated herein by reference. The teachings of these patents do not disclose preparing tissue/device with scaffolds or collagen matrix with desirable porosity for use in tissue engineering, wherein the raw material source for tissue engineering is chemically modified by genipin, genipin derivatives or its analog with acceptably minimal cytotoxicity.

Noishiki et al. in U.S. Pat. No. 4,806,595 discloses a tissue treatment method by a crosslinking agent, polyepoxy compounds. Collagens used in that patent include an insoluble collagen, a soluble collagen, an atelocollagen prepared by removing telopeptides on the collagen molecule terminus using protease other than collagenase, a chemically modified collagen obtained by succinylation or esterification of above-described collagens, a collagen derivative such as gelatin, a polypeptide obtained by hydrolysis of collagen, and a natural collagen present in natural tissue (ureter, blood vessel, pericardium, heart valve, etc.) The Noishiki et al. patent is incorporated herein by reference. "Collagen matrix" in the present invention is collectively used referring to the above-mentioned collagens, collagen species, collagen in natural tissue, and collagen in a biological implant preform.

Voytik-Harbin et al. in U.S. Pat. No. 6,264,992 discloses submucosa as a growth substrate for cells. More particularly, the submucosa is enzymatically digested and gelled to form a shape retaining gel matrix suitable for inducing cell proliferation and growth both in vivo and in vitro. The Voytik-Harbin et al. patent is incorporated herein by reference. Collagen matrix chemically modified or treated by genipin of the present invention may serve as a shapeable raw material for making a biological implant preform adapted for inducing cell proliferation and ingrowth, but also resisting enzymatic degradation, both in vivo and in vitro.

Cook et al. in U.S. Pat. No. 6,206,931 discloses a graft prosthesis material including a purified, collagen-based matrix structure removed from a submucosa tissue source, wherein the submucosa tissue source is purified by disinfection and removal steps to deactivate and remove contaminants. The Cook et al. patent is incorporated herein by reference. Similarly, a collagen-based matrix structure, also known as "collagen matrix" in this disclosure, may serve as a biomaterial adapted for medical device use after chemical modification by genipin of the present invention.

Levene et al. in U.S. Pat. No. 6,103,255 discloses a porous polymer scaffold for tissue engineering, whereby the scaffold is characterized by a substantially continuous solid phase, having a highly interconnected bimodal distribution of open pore sizes. The Levene et al. patent is incorporated herein by reference. The present invention discloses biological scaffolds by acellular process and acidic/enzymatic treatment adapted for tissue engineering. Additional benefits of genipin tissue treatment for reduced antigenicity, reduced cytotoxicity and enhanced biodurability are disclosed in the present invention.

Bell in U.S. Pat. No. 6,051,750, No. 5,893,888, and No. 5,800,537 discloses method and construct for producing graft tissue from extracellular matrix, wherein the matrix particulates are seeded with living human cells or fused to constitute composites of various shape. The Bell patents are incorporated herein by reference. A collagen matrix with genipin treatment of the present invention enables a building material to constitute composites of various shape, size of a medical prosthesis or biological implants.

EXAMPLE 1

Tissue Specimen Preparation

In one embodiment of the present invention, bovine pericardia procured from a slaughterhouse are used as raw materials. The procured pericardia are transported to the laboratory in a cold normal saline. In the laboratory, the pericardia are first gently rinsed with fresh saline to remove excess blood on tissue. Adherent fat is then carefully trimmed from the pericardial surface. The cleaned/trimmed pericardium before acellular process is herein coded specimen-A. The procedure used to remove the cellular components from bovine pericardia is adapted from a method developed by Courtman et al (J Biomed Mater Res 1994; 28:655–66), which is also referred to herein as "an acellularization process". A portion of the trimmed pericardia is then immersed in a hypotonic tris buffer (pH 8.0) containing a protease inhibitor (phenylmethyl-sulfonyl fluoride, 0.35 mg/L) for 24 hours at 4° C. under constant stirring. Subsequently, they are immersed in a 1% solution of Triton X-100 (octylphenoxypolyethoxyethanol; Sigma Chemical, St. Louis, Mo., USA) in tris-buffered salt solution with protease inhibition for 24 hours at 4° C. under constant stirring. Samples then are thoroughly rinsed in Hanks' physiological solution and digested with DNase and RNase at 37° C. for 1 hour. This is followed by a further 24-hour extraction with Triton X-100 in tris buffer. Finally, all samples are washed for 48 hours in Hanks' solution and the acellular sample is coded specimen-B. Light microscopic examination of histological sections from extracted tissue revealed an intact connective tissue matrix with no evidence of cells.

A portion of the acellular tissue of bovine pericardia (specimen-B) is further treated with 1% acetic acid at room temperature for one hour. The acidic component is thereafter removed from the tissue by lyophilization at about –50° C. for 24 hours, followed by thorough rinse with filtered water to obtain the acellular pericardia having enlarged pore or added porosity. The tissue is stored in phosphate buffered saline (PBS, 0.01M, pH 7.4, Sigma Chemical), which tissue is coded specimen-C. The procedure of acetic acid treatment to add porosity is referred herein as "acid treatment". Similar results could be achieved by following the acid treatment with other diluted acid solution, such as nitric acid or the like, at the comparable acidity or pH vales.

The mechanism of increasing the tissue porosity treated by a mild acidic solution lies in the effect of [$H^+$] or [$OH^-$] values on the collagen fibers matrix of the acellular tissue. It is postulated and disclosed that acellular tissue treated with a base solution (i.e., a solution pH value greater than 7.0) could have the same effect upon enlarged pores or added porosity.

A portion of the bovine pericardia tissue post-acid treatment (i.e., specimen-C) is further treated with enzymatic collagenase as follows. Add 0.01 gram of collagenase to a beaker of 40 ml TES buffer and incubate the specimen-C pericardia tissue at 37° C. for 3 hours. The sample is further treated with 10 mM EDTA solution, followed by thorough rinse. The tissue is stored in phosphate buffered saline (PBS, 0.01M, pH 7.4, Sigma Chemical), which tissue is coded specimen-D. The procedure of collagenase treatment to add porosity is referred herein as "enzyme treatment".

EXAMPLE 2

Tissue Specimen Crosslinking

The cellular tissue (specimen-A) and acellular tissue (specimen-B) of bovine pericardia are fixed in 0.625% aqueous glutaraldehyde (Merck KGaA, Darmstadt, Germany) and are coded as specimen-A/GA and specimen-B/GA, respectively. Furthermore, the cellular tissue (specimen-A) and acellular tissue (specimen-B, specimen-C, and specimen-D) of bovine pericardia are fixed in genipin (Challenge Bioproducts, Taiwan) solution at 37° C. for 3 days and are coded as specimen-A/GP, specimen-B/GP, specimen-C/GP, and specimen-D/GP, respectively. The aqueous glutaraldehyde and genipin solutions used are buffered with PBS. The amount of solution used in each fixation was approximately 200 mL for a 10×10 cm bovine pericardium. After fixation, the thickness of each studied group is determined using a micrometer (Digimatic Micrometer MDC-25P, Mitutoyo, Tokyo, Japan). Subsequently, the fixed cellular and acellular tissue are sterilized in a graded series of ethanol solutions with a gradual increase in concentration from 20 to 75% over a period of 4 hours. Finally, the test tissue is thoroughly rinsed in sterilized PBS for approximately 1 day, with solution change several times, and prepared for tissue characterization as well as a subcutaneous study. The chemical structures of the crosslinking agents (genipin and glutaraldehyde as control) used in the study are shown in FIG. 1.

In the present invention, the terms "crosslinking", "fixation", "chemical modification", and/or "chemical treatment" for tissue are used interchangeably.

Though the methods for removing cells from cellular tissue and/or acid treatment, base treatment, enzyme treatment to enlarge pores are well known to those who are skilled in the art, it is one object of the present invention to provide an acellular biological scaffold chemically treated with a naturally occurring crosslinking agent, genipin, that is configured and adapted for tissue regeneration, and/or tissue engineering in biomedical applications with acceptable cytotoxicity and reduced enzymatic degradation.

Figure 2:
FIG. 2 are photomicrographs of H&E stained tissue for (a) specimen-A, cellular tissue; (b) specimen-B, acellular tissue; (c) specimen-C, the acid treated acellular tissue; and (d) specimen-D, the enzyme treated acellular tissue.
Figure 2:
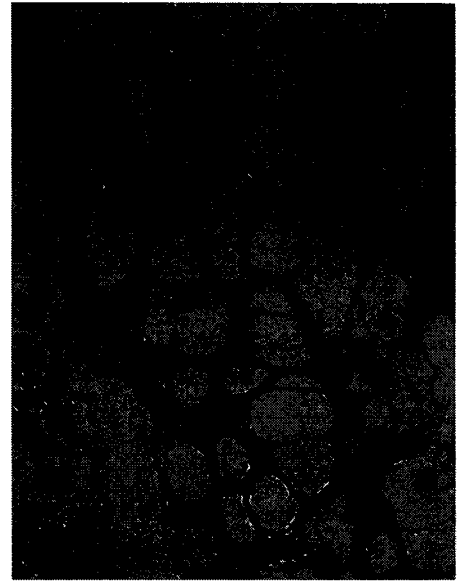
Figure 2:
Figure 2:
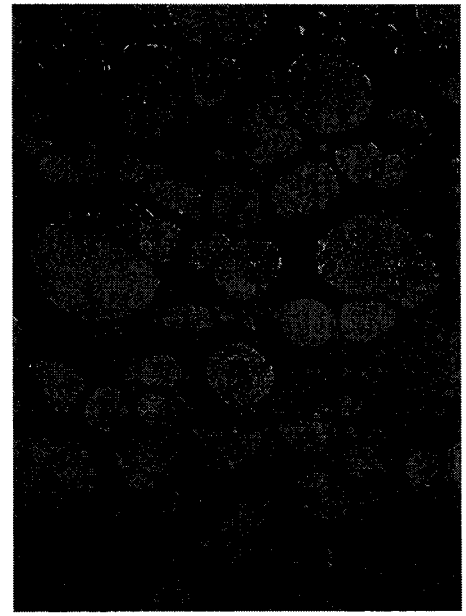

FIG. 2 shows photomicrographs of H&E (hematoxylin and eosin) stained tissue for (a) specimen-A, cellular tissue; (b) specimen-B, acellular tissue; (c) specimen-C, the acid treated acellular tissue; and (d) specimen-D, the enzyme treated acellular tissue. As shown in FIG. 2(a), the bovine pericardia prior to cell extraction shows a number of intact cells with identifiable cell nuclei embedded within the connective tissue matrices. In contrast, the extracted tissue revealed an intact connective tissue matrix with no evidence of cells (FIGS. 2(b)–2(d)). Some open spaces within the acellular tissue are apparent with acid treated specimen-C and enzyme treated specimen-D.

Figure 3:
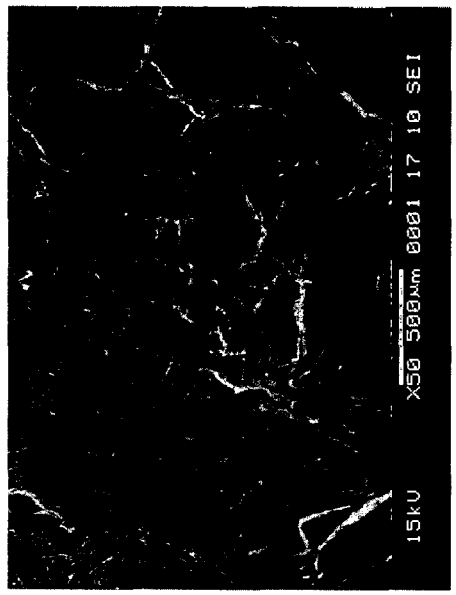
FIG. 3 shows the SEM of bovine pericardia tissue for (a) specimen-A, cellular tissue; (b) specimen-B, acellular tissue; (c) specimen-C, the acid treated acellular tissue; and (d) specimen-D, the enzyme treated acellular tissue.
Figure 3:
Figure 3:
Figure 3:
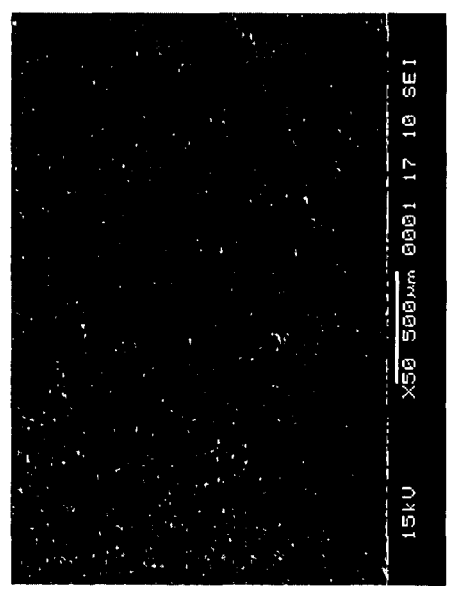

FIG. 3 shows the SEM (scanning electron microscopy) of bovine pericardia tissue for (a) specimen-A, cellular tissue; (b) specimen-B, acellular tissue; (c) specimen-C, the acid treated acellular tissue; and (d) specimen-D, the enzyme treated acellular tissue. The enzyme treated specimen-D shows several enlarged pores up to a couple of hundred microns, which would serve as a scaffold for enhanced tissue infiltration in tissue engineering.

Figure 4:
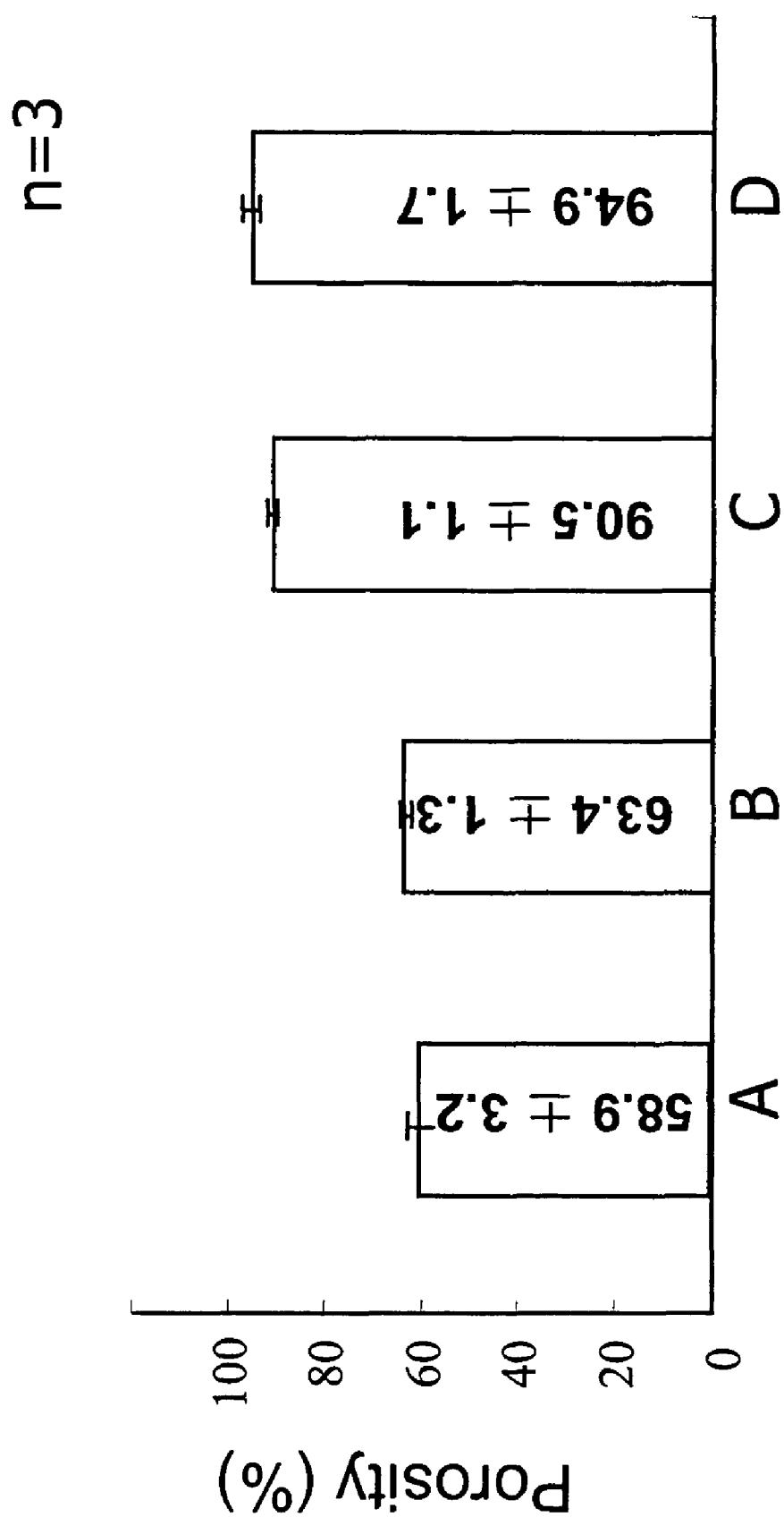
FIG. 4 shows porosity of bovine pericardia tissue for (a) specimen-A, cellular tissue; (b) specimen-B, acellular tissue; (c) specimen-C, the acid treated acellular tissue; and (d) specimen-D, the enzyme treated acellular tissue.

FIG. 4 shows porosity of bovine pericardia tissue for (a) specimen-A, cellular tissue; (b) specimen-B, acellular tissue; (c) specimen-C, the acid treated acellular tissue; and (d) specimen-D, the enzyme treated acellular tissue. "Porosity" is defined as the fraction of the void over the total apparent volume. The overall porosity of the acid treated and enzyme treated acellular tissue is substantial higher than the control cellular tissue. It is suggested that a tissue scaffold of the specimen-C or specimen-D type is desirable in tissue engineering applications for tissue infiltration or cells ingrowth.

EXAMPLE 3

Comparison of Glutaraldehyde and Genipin Crosslinking

Figure 5:
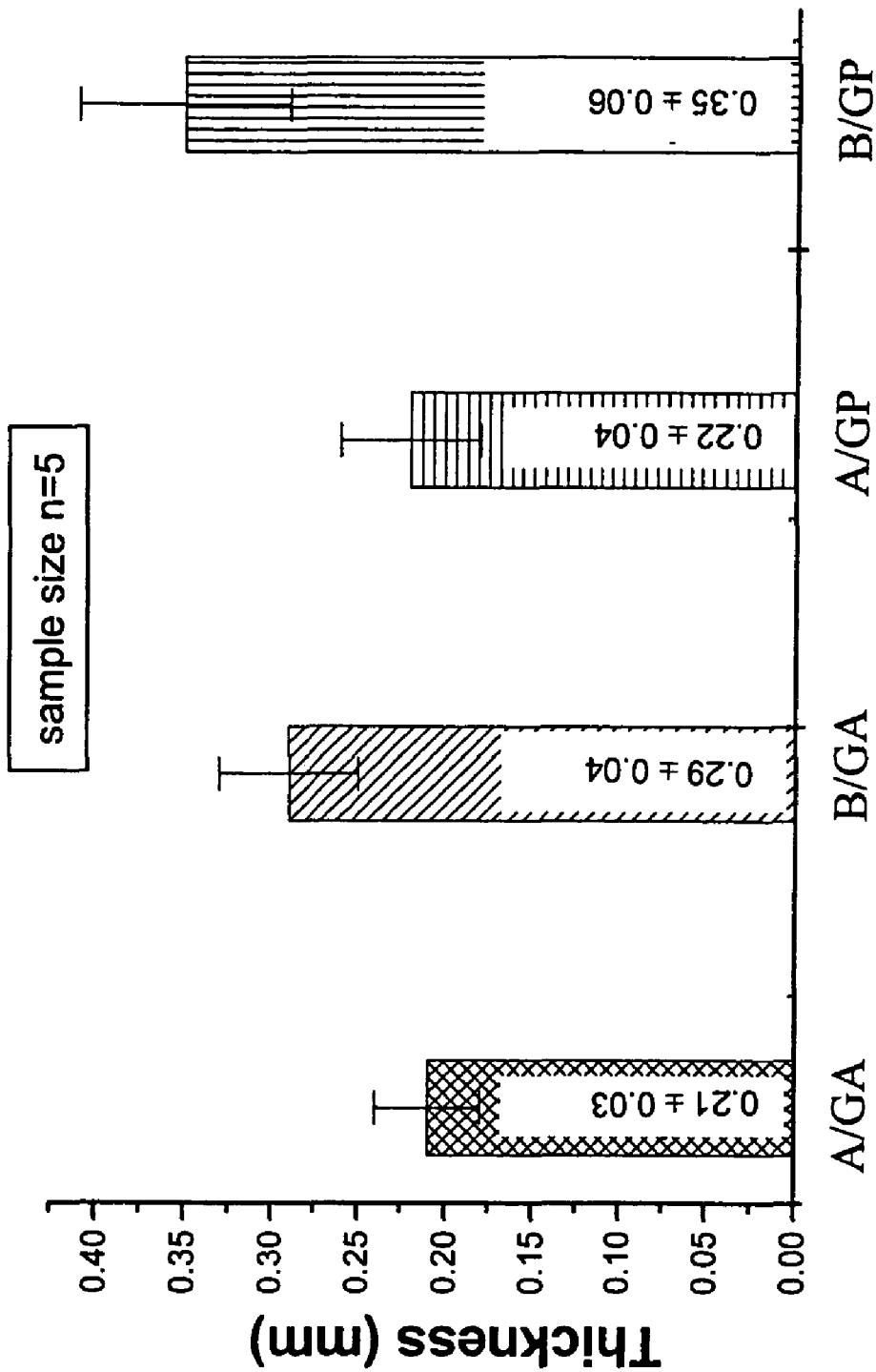
FIG. 5 shows thickness of the glutaraldehyde-fixed cellular tissue (A/GA), the glutaraldehyde-fixed acellular tissue (B/GA), the genipin-fixed cellular tissue (A/GP), and the genipin-fixed acellular tissue (B/GP) before implantation.

Pericardia tissue chemically treated with glutaraldehyde and genipin shows different characteristics and biocompatibility. FIG. 5 shows thickness of the glutaraldehyde-fixed cellular tissue (A/GA), the glutaraldehyde-fixed acellular tissue (B/GA), the genipin-fixed cellular tissue (A/GP), and the genipin-fixed acellular tissue (B/GP) before implantation. In general, the acellular tissue shows increased tissue thickness by either type of crosslinking (with glutaraldehyde or genipin) as compared to the control cellular tissue. It is further noticed that genipin-fixed acellular tissue shows the highest tissue thickness among the samples characterized, probably due to enhanced water absorption. This high tissue thickness of genipin-fixed acellular tissue is desirable for tissue engineering in vivo or in vitro in medical devices, such as an extended-release drug delivery device, vascular or skin graft, or orthopedic prosthesis of bone, ligament, tendon, and cartilage.

Figure 6:
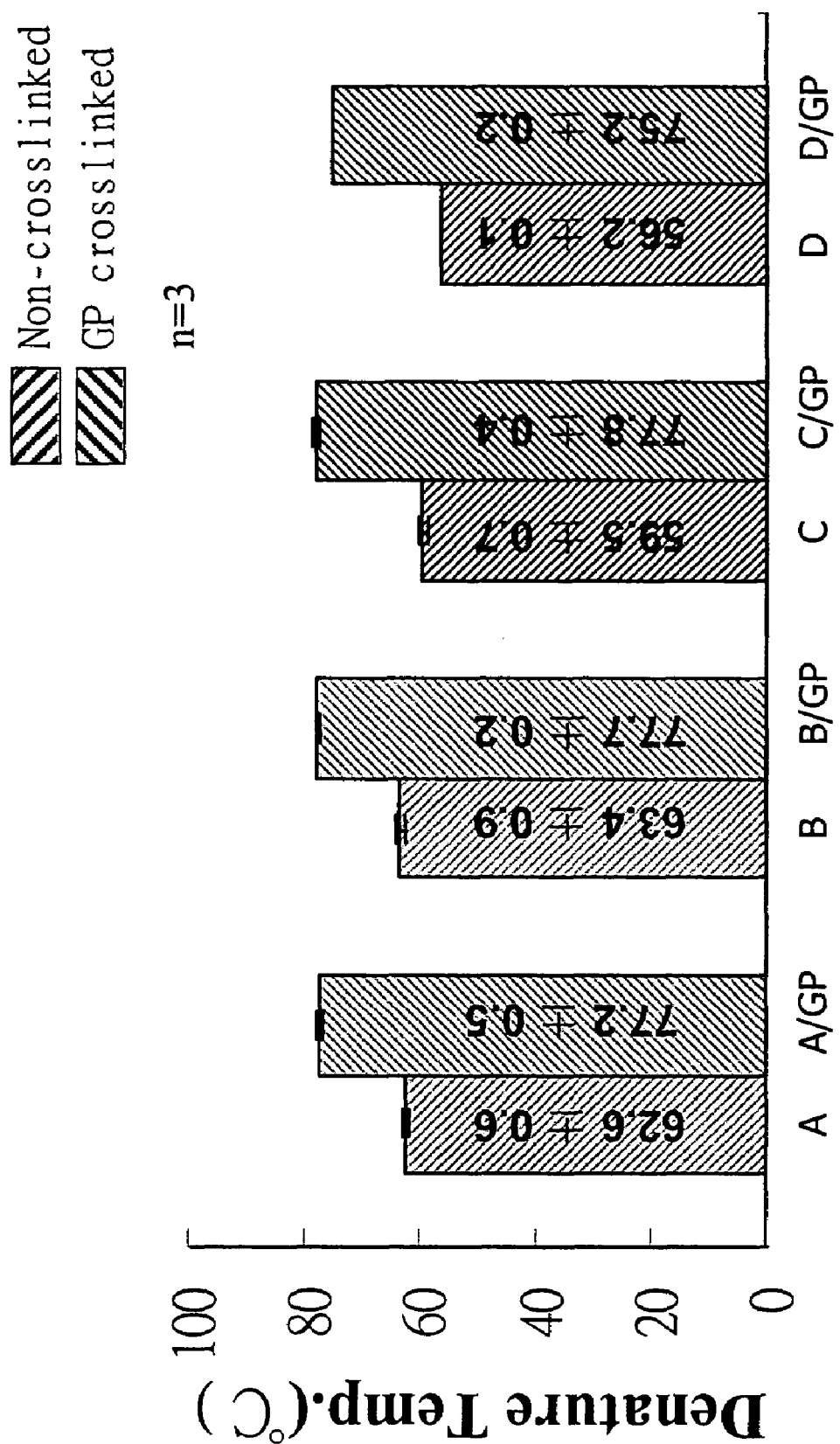
FIG. 6 show denaturation temperature values of the non-crosslinked and genipin-crosslinked bovine pericardia tissue for (a) specimen-A, cellular tissue; (b) specimen-B, acellular tissue; (c) specimen-C, the acid treated acellular tissue; and (d) specimen-D, the enzyme treated acellular tissue.

To characterize the degree of tissue crosslinking, denature temperatures are measured on the non-crosslinked and genipin-crosslinked bovine pericardia tissue for (a) specimen-A, cellular tissue; (b) specimen-B, acellular tissue; (c) specimen-C, the acid treated acellular tissue; and (d) specimen-D, the enzyme treated acellular tissue (FIG. 6). The denaturation temperatures of specimens of each studied group before implantation and those retrieved at distinct duration postoperatively are measured in a Perkin Elmer differential scanning calorimeter (Model DSC-7, Norwalk, Conn., USA). This technique was widely used in studying the thermal transitions of collagenous tissues. Details of the methodology used in the denaturation temperature measurement were described elsewhere (J Biomed Mater Res 1998; 42:560–567). As shown in FIG. 6, the denature temperatures in all four types of genipin (GP) crosslinked pericardia tissue are higher as expected than their control non-crosslinked counterparts.

Figure 7:
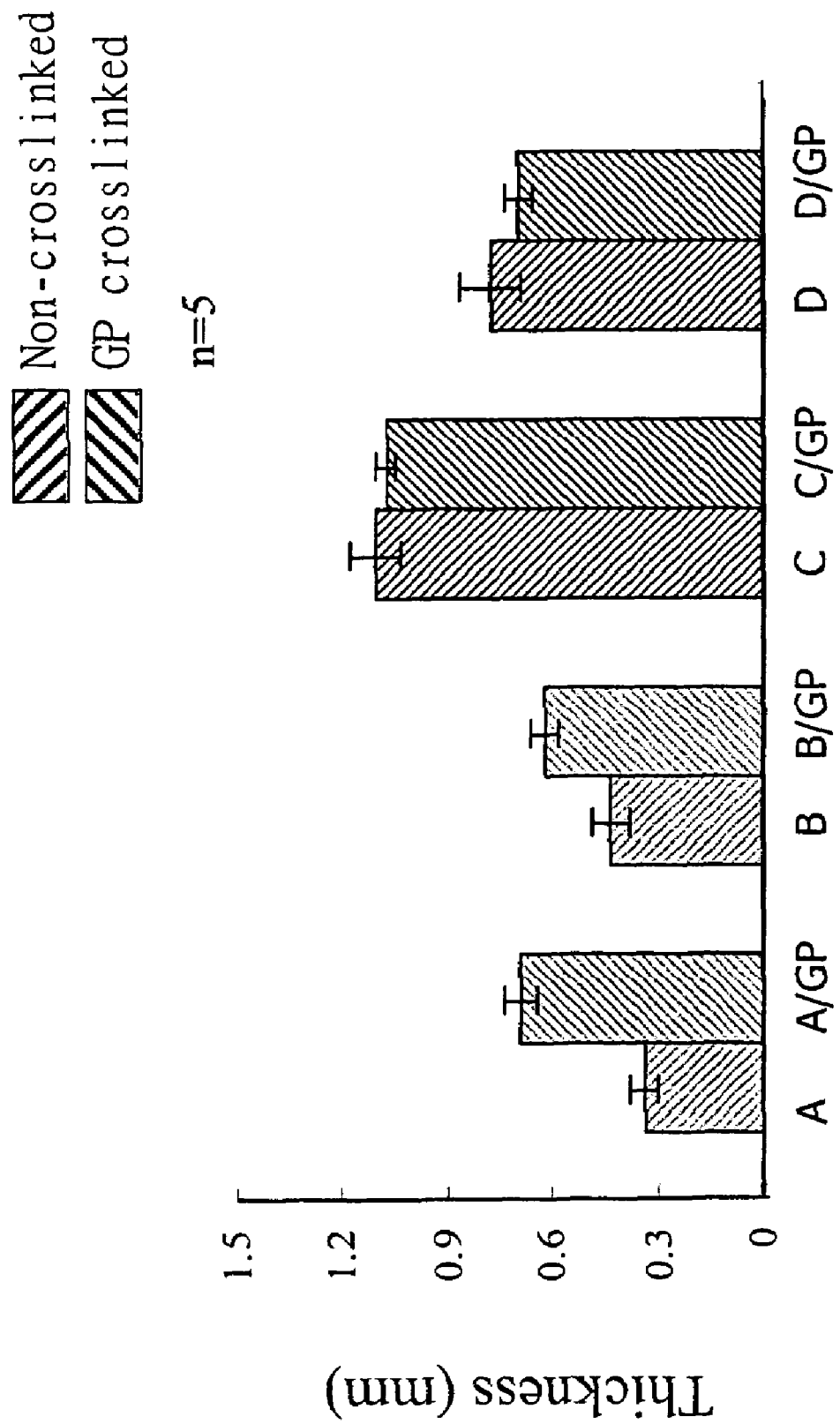
FIG. 7 shows thickness of the bovine pericardia tissue before and after genipin crosslinking for (a) specimen-A, cellular tissue; (b) specimen-B, acellular tissue; (c) specimen-C, the acid treated acellular tissue; and (d) specimen-D, the enzyme treated acellular tissue.

FIG. 7 shows thickness of the bovine pericardia tissue before and after genipin crosslinking for (a) specimen-A, cellular tissue; (b) specimen-B, acellular tissue; (c) specimen-C, the acid treated acellular tissue; and (d) specimen-D, the enzyme treated acellular tissue. For example, a genipin-crosslinked specimen-A is designated as specimen-A/GP, and so forth. It is suggested that thicker tissue is normally due to higher water content or water absorption capability. It implies that the loose extracellular space temporarily occupied by water in acid treated pericardia tissue (in either non-crosslinked tissue or genipin crosslinked tissue) would be desirable for tissue engineering applications in an extended-release drug delivery device, vascular or skin graft, or orthopedic prosthesis, such as bone, ligament, tendon, cartilage, and muscle. The biological tissue material with added porosity may comprise steps of removing cellular material from a natural tissue and crosslinking the natural tissue with a crosslinking agent, wherein the natural tissue is selected from a group consisting of a porcine valve, a bovine jugular vein, a bovine pericardium, an equine pericardium, a porcine pericardium, and submucosal tissue.

EXAMPLE 4

Animal Implant Study

Figure 8:
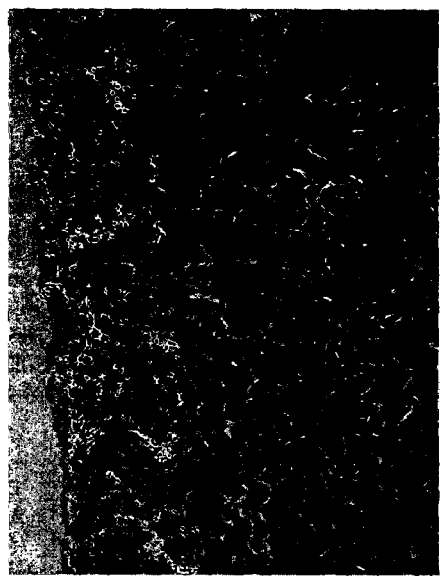
FIG. 8 are photomicrographs of H&E stained genipin-crosslinked tissue for (a) specimen-A/GP, cellular tissue; (b) specimen-B/GP, acellular tissue; (c) specimen-C/GP, the acid treated acellular tissue; and (d) specimen-D/GP, the enzyme treated acellular tissue retrieved at 3-day postoperatively.
Figure 8:
Figure 8:
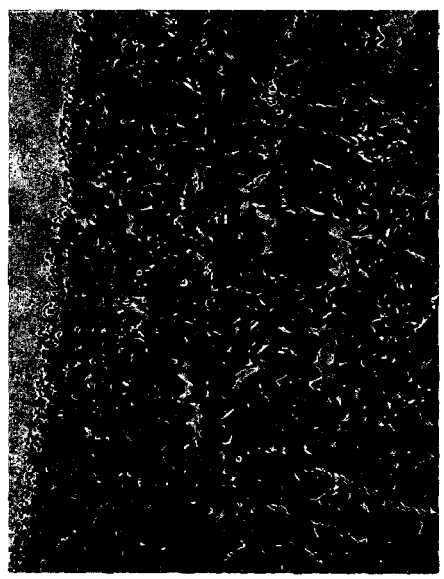
Figure 8:

The cellular and acellular tissue fixed with glutaraldehyde and genipin from Example 2 were implanted subcutaneously in a growing rat model (4-week-old male Wistar) under aseptic conditions. Each test sample was approximately 1 cm by 2 cm coupon. In a first study, genipin-crosslinked tissue for specimen-A/GP, specimen-B/GP, specimen-C/GP, and specimen-D/GP are implanted. FIG. 8 shows photomicrographs of H&E stained genipin-crosslinked tissue for (a) specimen-A/GP, cellular tissue; (b) specimen-B/GP, acellular tissue; (c) specimen-C/GP, the acid treated acellular tissue; and (d) specimen-D/GP, the enzyme treated acellular tissue: all retrieved at 3-day postoperatively. It is apparent that cells infiltration into the enlarged pores of the enzyme treated specimen-D/GP is quite visible and evident. The samples used for light microscopy were fixed in 10% phosphate buffered formalin for at least 3 days and prepared for histological examination. In the histological examination, the fixed samples were embedded in paraffin and sectioned into a thickness of 5 $\mu$m and then stained with hematoxylin and eosin (H&E). The stained sections of each test sample then are examined using light microscopy (Nikon Microphoto-FXA) for tissue inflammatory reaction and photographed with a 100 ASA Kodachrome film.

Figure 9:
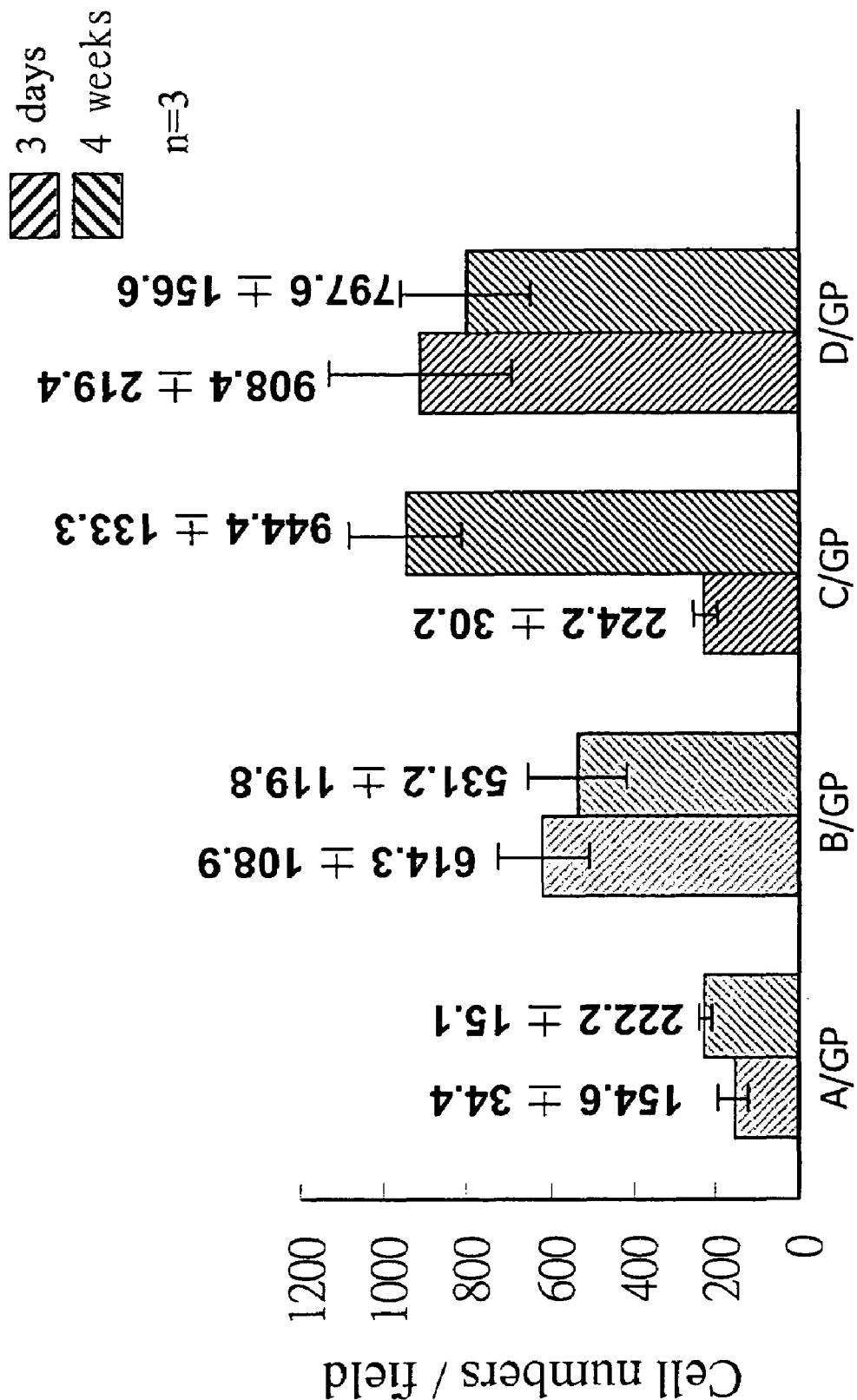
FIG. 9 are cells infiltration extents of genipin-crosslinked bovine pericardia tissue for (a) specimen-A/GP, cellular tissue; (b) specimen-B/GP, acellular tissue, (c) specimen-C/GP, the acid treated acellular tissue; and (d) specimen-D/GP, the enzyme treated acellular tissue retrieved at 3 days and 4-week postoperatively.

In the first study, genipin-crosslinked tissue for (a) specimen-A/GP, cellular tissue; (b) specimen-B/GP, acellular tissue; (c) specimen-C/GP, the acid treated acellular tissue; and (d) specimen-D/GP, the enzyme treated acellular tissue are retrieved at 3-day and 4 weeks postoperatively. The cell numbers per field (on a reference basis) are counted and shown in FIG. 9. At 4 weeks implantation, both specimen-C/GP and specimen-D/GP show significant higher cells infiltration than the tissue samples without enlarged pores (i.e., specimen-A/GP or specimen-B/GP).

A second study is conducted for comparing the effect of glutaraldehyde (GA)-fixed and genipin (GP)-fixed tissue samples on their ultimate tensile strength. The implanted test samples then were retrieved at 3-day, 1-week, 4-week, 12-week, 24-week, and 52-week postoperatively. At retrieval, the appearance of each retrieved sample first was grossly examined and photographed. The samples were then processed for light microscopy or tensile strength measurement.

The tensile strength values of specimens of each studied group before implantation and those retrieved at distinct implantation duration were determined by uniaxial measurements using an Instron material testing machine (Mini 44, Canton, Mass., USA) at a constant speed of 10 mm/min.

Figure 10:
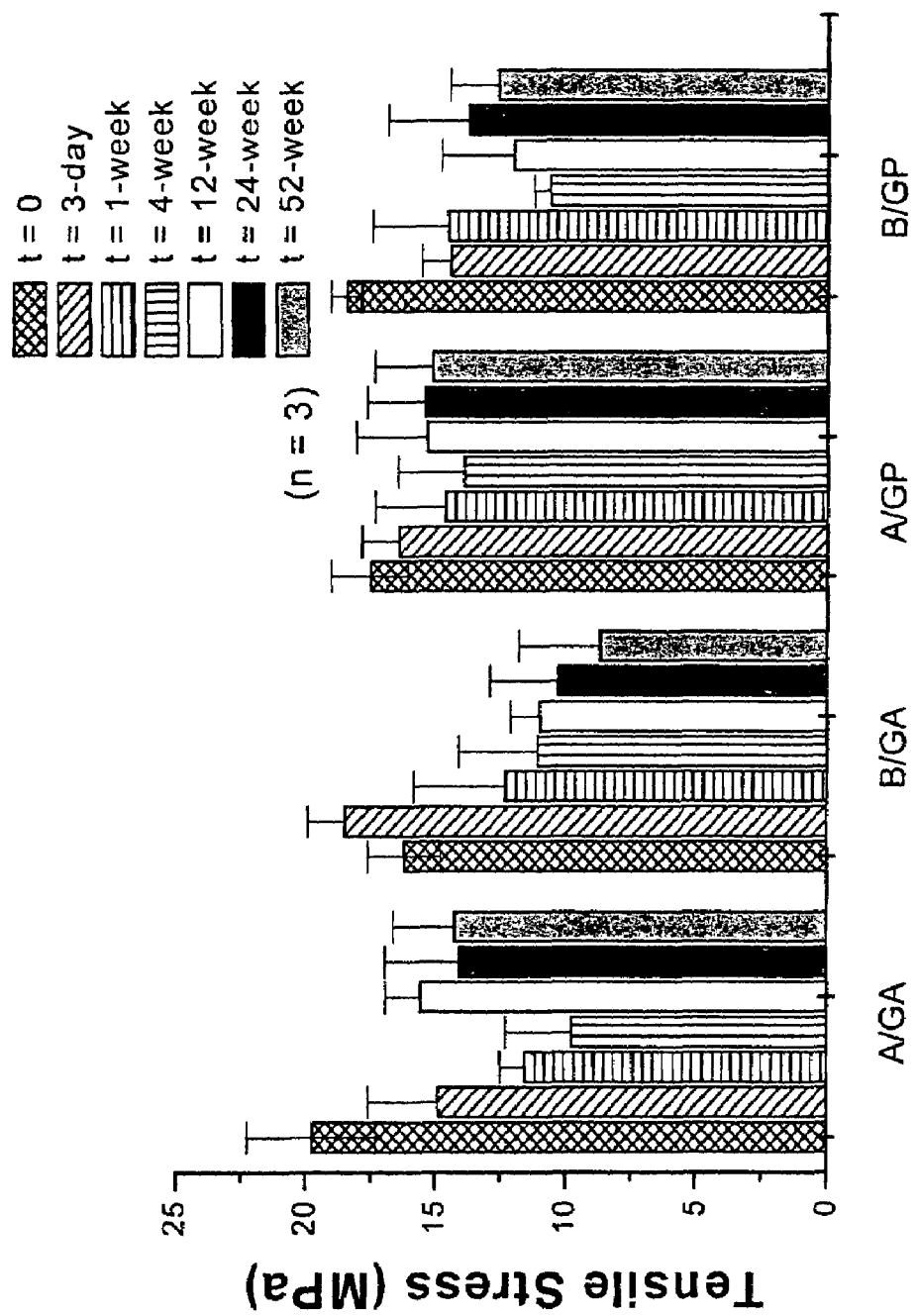
FIG. 10 are tensile-strength values of the glutaraldehyde-fixed cellular tissue (A/GA), the glutaraldehyde-fixed acellular tissue (B/GA), the genipin-fixed cellular tissue (A/GP), and the genipin-fixed acellular tissue (B/GP) before implantation and those retrieved at several distinct duration of post implantation.

As shown in FIG. 10, the tensile strength values of all test samples before implantation were comparable (P>0.05). It is found that the tensile-strength values of all test samples declined significantly with increasing the duration of implantation prior to 4-week postoperatively (P<0.05). However, with the exception of the glutaraldehyde-fixed acellular tissue, the tensile strength values of all other test samples increased steadily afterwards (P<0.05).

EXAMPLE 5

Gelatin Crosslinking Experiment

3-D Scaffold: Gelatin (0.8 g) dissolved in 7 mL phosphate buffered saline was crosslinked by 3 mL 1% genipin or 0.167% glutaraldehyde for 9 hours. The crosslinked gelatin was dried in an oven (37° C.) for 1 hour and then frozen at −30° C. for 9 hours. Finally, the frozen gelatin was lyophilized to create a 3-D scaffold. This represents one type of the "collagen matrix" as defined in the present invention.

In the cell culture, 16-mm-diameter test samples cut from the sterilized glutaraldehyde-fixed or genipin-fixed tissue were glued to the bottoms of the wells in a 24-well plate (the diameter of each well is about 16 mm) using a sterilized collagen solution. Subsequently, human fibroblasts (HFW) at $5 \times 10^4$ cells/well were seeded evenly on the surface of each test sample in DMEM with 10% FCS. The test samples in the wells then were removed at 3-day through 1-month after cell seeding. During this period, the growth medium was changed routinely. After cell culture, the test scaffolds were washed with phosphate buffered saline (PBS) twice and surviving cell numbers were determined by the MTT assay (J Biomater Sci Polymer Edn 1999; 10:63–78).

As disclosed in a co-pending provisional application Ser. No. 60/314,195 filed Aug. 22, 2001 entitled CHEMICAL MODIFICATION OF ACELLULAR BIOMEDICAL MATERIAL WITH GENIPIN, entire contents of which are incorporated herein by reference, the structure of the genipin-fixed scaffold remained intact throughout the entire course of the experiment (up to 1-month after cell culture), while that of the glutaraldehyde-fixed scaffold was found collapsed in the culture medium at 7-day after cell seeding. The human fibroblasts cultured in the genipin-crosslinked scaffold were significantly greater than the glutaraldehyde-crosslinked scaffold throughout the entire course of the experiment as observed in the MTT assay. This indicates that the cellular compatibility of the genipin-crosslinked scaffold is superior to that of the glutaraldehyde-crosslinked scaffold.

The experiment presents the cellular compatibility of a 3-D porous scaffold made from gelatin chemically modified or crosslinked by genipin. The glutaraldehyde-fixed counterpart was used as control. The results obtained indicate that the genipin-crosslinked scaffold had a better cellular compatibility than its glutaraldehyde-fixed counterpart. Additionally, the glutaraldehyde-crosslinked scaffold was found collapsed by 7-day after cell culture, while the genipin-crosslinked scaffold remained intact up to 1-month after cell culture. It is hereby disclosed that the genipin-fixed porous scaffold when configured and adapted for tissue regeneration or tissue engineering comprising steps of removing cellular material from a natural tissue and crosslinking the natural tissue with genipin is desirable, wherein the 3-D scaffold is characterized by reduced antigenicity, reduced immunogenicity and reduced enzymatic degradation upon placement inside a patient's body. The porosity of the scaffold tissue is increased at least 5% over that of the nature tissue adapted for promoting tissue regeneration or tissue engineering.

As disclosed and outlined in the co-pending provisional application Ser. No. 60/314,195 by the present inventors, the degrees in inflammatory reaction in the animal studies for the genipin-fixed cellular and acellular tissue were significantly less than their glutaraldehyde-fixed counterparts. Additionally, it was noted that the inflammatory reactions for the glutaraldehyde-fixed cellular and acellular tissue lasted significantly longer than their genipin-fixed counterparts. These findings indicated that the biocompatibility of the genipin-fixed cellular and acellular tissue is superior to the glutaraldehyde-fixed cellular and acellular tissue. It is hypothesized that the lower inflammatory reactions observed for the genipin-fixed cellular and acellular tissue may be due to the lower cytotoxicity of their remaining residues, as compared to the glutaraldehyde-fixed counterparts. In our previous study, it was found that genipin is significantly less cytotoxic than glutaraldehyde (J Biomater Sci Polymer Edn 1999; 10:63–78). The cytotoxicity observed for the glutaraldehyde-fixed cellular and acellular tissue seems to result from a slow leaching out of unreacted glutaraldehyde as well as the reversibility of glutaraldehyde-crosslinking. It was observed that when concentrations above 0.05% glutaraldehyde were used to crosslink materials, a persistent foreign-body reaction occurred (J Biomater Sci Polymer Edn 1999; 10:63–78).

In the study (co-pending provisional application Ser. No. 60/314,195), it was found that the inflammatory cells were mostly surrounding the cellular tissue, while they were able to infiltrate into the outer layers of the acellular tissue for both the glutaraldehyde-fixed and genipin-fixed groups. As aforementioned, as compared to the cellular tissue, the acellular tissue formed a decreased density of the structural fiber components due to the increase in their thickness (FIG. 5). In addition, after cell extraction, it left more open spaces in the acellular tissue (FIG. 4). As a result, the inflammatory cells were able to infiltrate into the acellular tissue. This significantly increases the contact area between the host immune system (the inflammatory cells) and the foreign material (the acellular-tissue matrix). Consequently, the degrees in inflammatory reaction for the acellular tissue were consistently grater than the cellular tissue.

Figure 11:
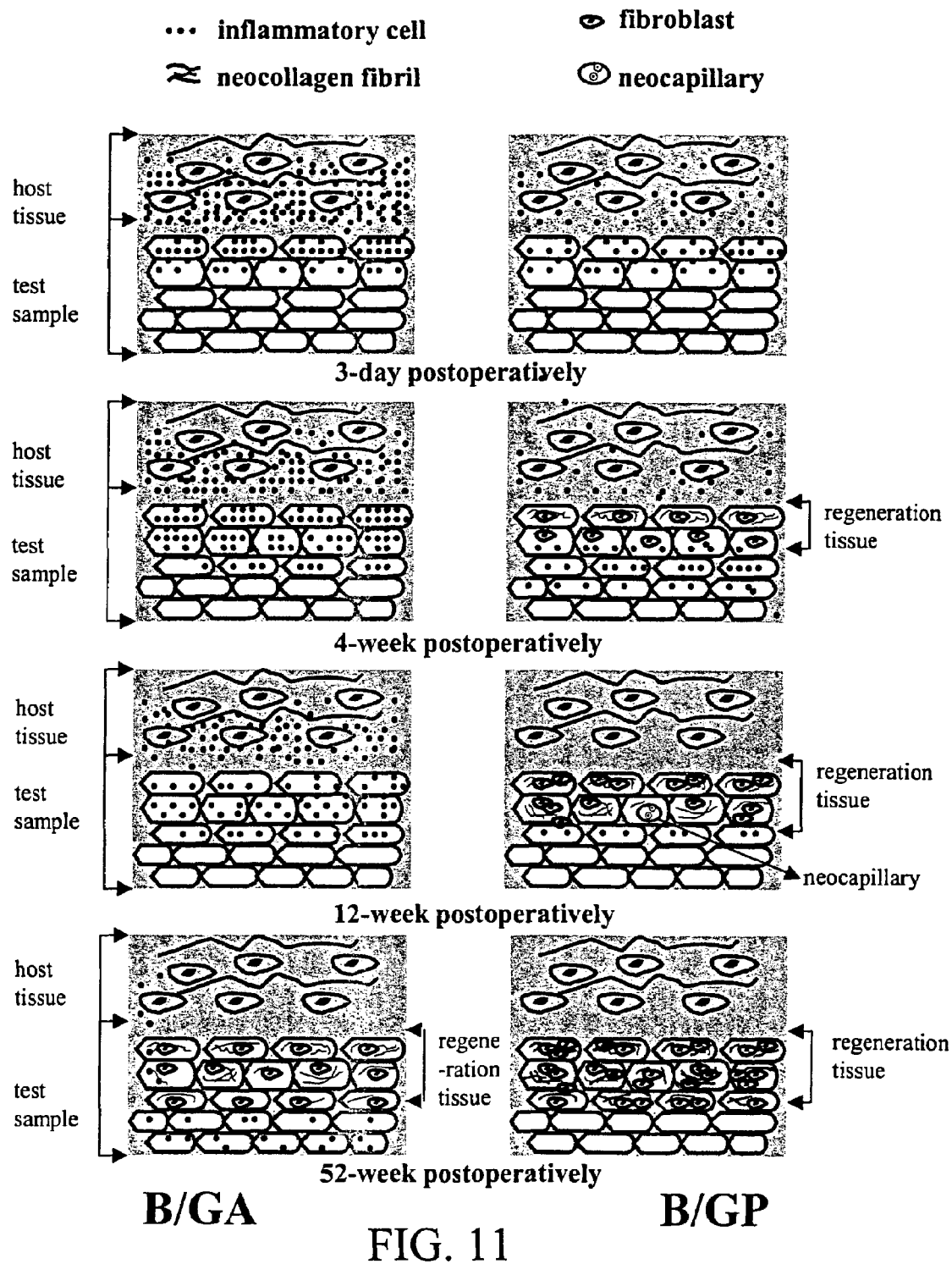
FIG. 11 is an illustration of the suggested mechanism of tissue regeneration in the outer layers of the acellular tissue as disclosed in the present invention wherein B/GA denotes the glutaraldehyde-fixed acellular tissue and B/GP denotes the genipin-fixed acellular tissue.

As the cells were able to infiltrate into the outer layers of the acellular tissue, tissue regeneration from the host was observed in this area. FIG. 11 illustrates a suggested mechanism of tissue regeneration in the outer layers of the acellular tissue as per the findings disclosed in the present invention and co-pending provisional application Ser. No. 60/314,195. Once the inflammatory cells infiltrated into the acellular tissue matrix, the enzymes (collagenase and other proteases) secreted by macrophages might start to degrade the fibrous proteins. This allowed fibroblasts from the host tissue (rat's tissue in one example) to migrate into the outer layer of the acellular tissue and to secrete neocollagen fibrils. As duration of implantation progresses, angiogenesis (neocapillaries) occurs. Thus more fibroblasts from the host tissue migrate into the acellular tissue matrix and therefore more neocollagen fibrils are produced. As a result, the most outer layers of the glutaraldehyde-fixed and genipin-fixed acellular tissue observed at 52-week postoperatively were the new tissue regenerated from the host. The tissue regeneration rate observed in the outer layer of the genipin-fixed acellular tissue matrix was significantly faster than its glutaraldehyde-fixed counterpart (FIG. 11).

In conclusion, the results as disclosed in the present invention indicate that the degrees in inflammatory reaction for the genipin-fixed cellular and acellular tissue are significantly less than their glutaraldehyde-fixed counterparts. The acellular tissue provides a natural microenvironment for cell migration to regenerate tissue. The tissue regeneration rate for the genipin-fixed acellular tissue is significantly faster than its glutaraldehyde-fixed counterpart. And this faster tissue regeneration enables a genipin-fixed acellular tissue suitable as a biological scaffold configured and adapted for tissue regeneration or tissue engineering, wherein the scaffold is characterized by reduced antigenicity, reduced immunogenicity and reduced enzymatic degradation upon placement inside a patient's body.

It is hereby disclosed that a method of preparing a biological scaffold configured and adapted for tissue regeneration or tissue engineering comprises steps of removing cellular material from a natural tissue or collagen matrix; and chemically modifying the acellular tissue or collagen matrix with genipin. As defined, "genipin" in this invention is meant to refer to the naturally occurring compound as shown in FIG. 1 and its derivatives, analog, stereoisomers and mixtures thereof. The biological scaffold of the present invention may be characterized by reduced antigenicity, reduced immunogenicity and reduced enzymatic degradation upon placement inside a patient's body. The collagen matrix of the present invention may be selected from a group consisting of an insoluble collagen, a soluble collagen, an atelocollagen prepared by removing telopeptides on the collagen molecule terminus using protease other than collagenase, a chemically modified collagen obtained by succinylation or esterification of above-described collagens, a collagen derivative such as gelatin, a polypeptide obtained by hydrolysis of collagen, and a natural collagen present in natural tissue (ureter, blood vessel, pericardium, heart valve, etc.).

It is further disclosed that a biological scaffold for cells seeding, cell growth or cell proliferation may comprise a natural tissue devoid of cellular material and chemically modified by genipin. As indicated in FIG. 4, the porosity increase of the acellular specimen-B is 7.6% higher than its control cellular specimen-A. Furthermore, the porosity increase of the acid treated acellular tissue specimen-C and the porosity increase of the enzyme treated acellular tissue specimen-D are 53% and 61%, respectively higher than the porosity of the control cellular specimen-A. The biological scaffold may be characterized by an increase of the biological scaffold volume after treatment by at least 5%, preferably more than 10% of volume porosity change (FIG. 4). The "treatment" to make a biological tissue material or scaffold of the present invention may include the acellularization process, acid treatment, base treatment, and/or enzyme (e.g. protease) treatment processes. The biological tissue material is selected from a group consisting of a tissue valve, a tissue valve leaflet, a vascular graft, a ureter, a urinary bladder, pericardium, and a dermal graft.

It is another embodiment of the present invention to provide a tendon or ligament graft for use as connective tissue substitute, the graft being formed from a segment of connective tissue protein, wherein the segment is crosslinked with genipin, its analog or derivatives. The connective tissue protein may be collagen or pericardia patches that is substantially devoid of cells and porosity of the tissue graft is increased at least 5% adapted for promoting autogenous ingrowth into the graft. The process for using a tissue sheet to make a tendon or ligament graft has been disclosed by Badylak et al. in U.S. Pat. No. 5,573,784, No. 5,445,833, No. 5,372,821, No. 5,281,422, and so forth, the entire contents of which are incorporated herein by reference, which disclose a method for promoting the healing and/or regrowth of diseased or damaged tissue structures by surgically repairing such structures with a tissue graft construct prepared from a segment of intestinal submucosal tissue.

Further, Badylak et al. in U.S. Pat. No. 6,485,723, the entire contents of which are incorporated herein by reference, discloses an improved tissue graft construct comprising vertebrate submucosa delaminated from both the external smooth muscle layers and the luminal portions of the tunica mucosa and added primary cells, wherein the vertebrate submucosa comprises tunica submucosa delaminated from both the tunica muscularis and at least the luminal portion of the tunica mucosa of vertebrate intestinal tissue. With added porosity, it is herein provided a biological tissue material derived from submucosal tissue adapted for promoting tissue regeneration.

U.S. Pat. No. 6,506,398 issued to Tu (a co-inventor of the present invention), the entire contents of which are incorporated herein by reference, discloses a vascular graft comprising Vascular Endothelial Growth Factor (VEGF) and/or Platelet Derived Growth Factor (PDGF) for enhanced site-specific angiogenesis and methods thereof. At least one VEGF, PDGF or angiogenesis factor is incorporated into the vascular graft to facilitate enhanced angiogenesis so as the cells are stimulated to migrate to environments having higher concentration of growth factors and start mitosis. With added porosity, it is provided a biological tissue material with loaded growth factors adapted for promoting tissue regeneration, wherein the growth factor is selected from the group consisting of VEGF, VEGF 2, bFGF, VEGF121, VEGF165, VEGF189, VEGF206, PDGF, PDAF, TGF-$\beta$, PDEGF, PDWHF, and combination thereof.

Vascular endothelial growth factor (VEGF) is mitogenic for vascular endothelial cells and consequently is useful in promoting neovascularization (angiogenesis) and reendothelialization. Angiogenesis means the growth of new capillary blood vessels. Angiogenesis is a multi-step process involving capillary endothelial cell proliferation, migration and tissue penetration. VEGF is a growth factor having a cell-specific mitogenic activity. It would be desirable to employ a wound healing substrate incorporating a mitogenic factor having mitogenic activity that is highly specific for vascular endothelial cells following vascular graft surgery, balloon angioplasty or to promote collateral circulation. U.S. Pat. No. 5,194,596 discloses a method for producing VEGF while U.S. Pat. No. 6,040,157 discloses a specific VEGF-2 polypeptide. Both patents are incorporated herein by reference.

Gordinier et al. in U.S. Pat. No. 5,599,558 discloses a method of making a platelet releasate product and methods of treating tissues with the platelet releasate. Platelet derived growth factor (PDGF) is a well-characterized dimeric glycoprotein with mitogenic and chemoattractant activity for fibroblasts, smooth muscle cells and glial cells. In the presence of PDGF, fibroblasts move into the area of tissue needing repair and are stimulated to divide in the lesion space itself. It has been reported that the cells exposed to lower PDGF concentrations are stimulated to move to environments having higher concentrations of PDGF and divide. The patent is incorporated hereby by reference.

In some aspects, there is provided a method for promoting autogenous ingrowth of a biological tissue material comprising the steps of providing a natural tissue, removing cellular material from the natural tissue, increasing porosity of the natural tissue by at least 5%, loading an angiogenesis agent or autologous cells into the porosity, and crosslinking the natural tissue with a crosslinking agent. In one preferred embodiment, the angiogenesis agent is ginsenoside $Rg_1$, or selected from the group consisting of VEGF, VEGF 2, bFGF, VEGF121, VEGF165, VEGF189, VEGF206, PDGF, PDAF, TGF-$\beta$, PDEGF, PDWHF, polyepoxy compounds, and combination thereof.

Duckett et al. in U.S. Pat. No. 6,340,480, the entire contents of which are incorporated herein by reference, discloses a composition for promoting circulation, comprising an effective amount of L-arginine, ginseng and *Ziyphi fructus*, the constituents being administered to stimulate release of NO in the body. Some past studies with natural ingredients have shown that with natural medicines include ginseng, ginsenoside, and its purified derivative $Rg_1$ have a tendency to increase synthesis of NO levels. It has been shown that $Rg_1$ enhances the production of NO for killing certain tumor cells. See, e.g., Fan et al., Enhancement of Nitric Oxide Production from Activated Macrophages by a Purified Form of Ginsenoside ($Rg_1$), American Journal of Chinese Medicine, Vol. XXHI, Nos. 3–4. pp. 279–287 (1995 Institute for Advanced Research in Asian Science and Medicine).

Figure 12:
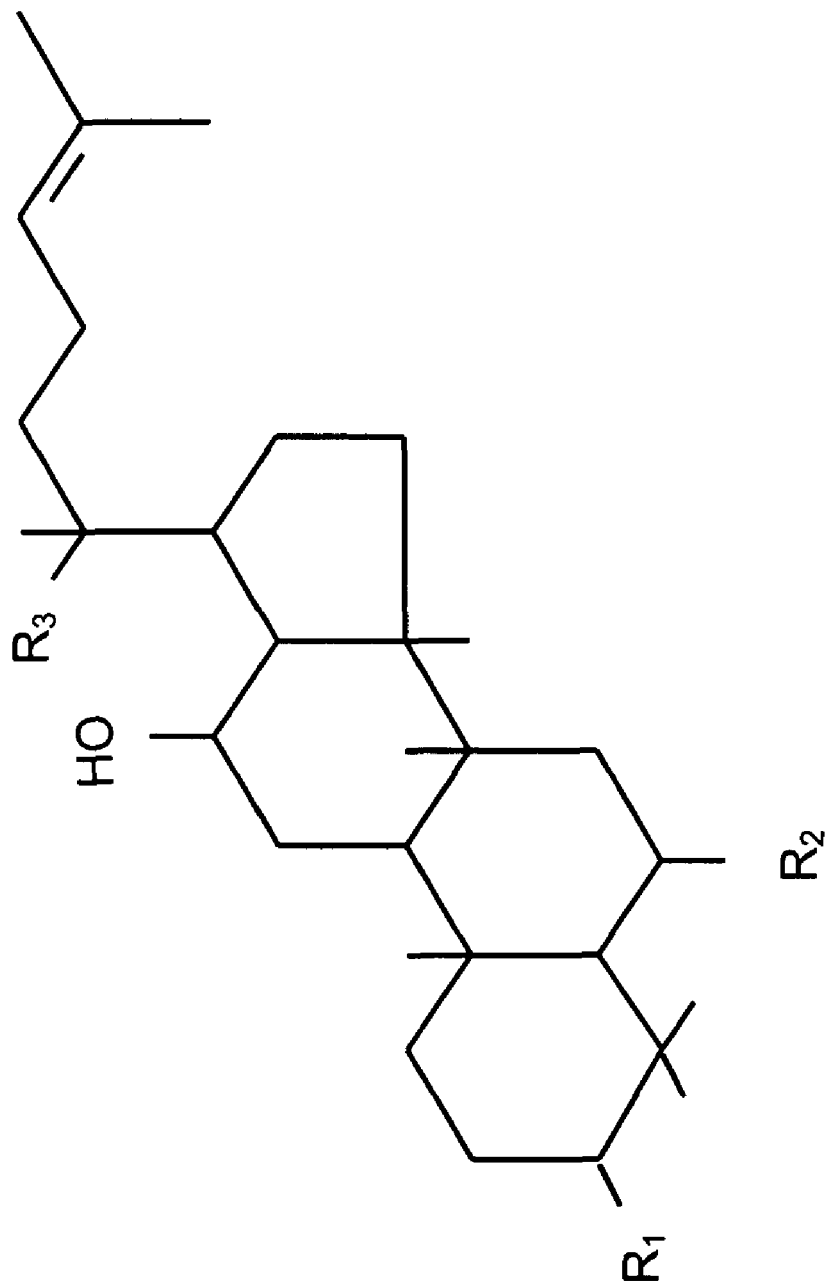
FIG. 12 is a chemical formula of ginsenoside $Rg_1$.

FIG. 12 shows a chemical formula of ginsenoside $Rg_1$, one of the principal active components of ginseng saponins which is isolated from the roots of *Panax ginseng*. In one embodiment as shown in FIG. 12, in which $R_1$=OH or O-Glc, $R_2$=H or O-Glc, $R_3$=O-Glc, wherein Glc designates a β-D glucopyranosyl group. $Rg_1$ is believed to stimulate vascular endothelial cells proliferation, and tube formation in a patient. Ginseng's therapeutic uses were recorded in the oldest Chinese pharmacopeia, Shen Nong Ben Cao Jing, written about two thousand years ago. Ginseng action is non-local and non-specific. In Asian medicine, ginseng is used as a tonic to revitalize the function of organism as a whole and replenish vital energy ("chi"). It is traditionally used as the best supplemental and restorative nature agent during convalescence and as a prophylactic to build resistance, reduces susceptibility to illness, and promotes health and longevity.

Other functions of ginseng are to stimulate mental and physical activity, strengthen and protect human organism, increase physical and mental efficiency and to prevent fatigue. Ginseng has good effect on the stomach, the brain, and the nervous system. Ginseng is effective for reflex nervous disease. Ginseng has also been found to have an anti-cancer effect. There are more than 30 kinds of ginsenosides, and each one function differently. Ginsenoside Rh2 has anti-tumor activity. Ginsenoside $Rg_1$ can enhance DNA and RNA formation, which may speed up the angiogenesis. In some aspect of the present invention, there is provided a method for promoting autogenous ingrowth of a biological tissue material comprising the steps of providing a natural tissue, removing cellular material from the natural tissue, increasing porosity of the natural tissue by at least 5%, loading an angiogenesis agent or autologous cells into the porosity, and crosslinking the natural tissue with a crosslinking agent. In one preferred embodiment, the angiogenesis agent is ginsenoside $RG_1$. In still another aspect of the invention, there is provided a method for treating cancer or tumor by implanting a biological tissue material comprising the steps of providing a natural tissue, removing cellular material from the natural tissue, increasing porosity of the natural tissue by at least 5%, loading a cancer/tumor antagonist agent into the porosity, and crosslinking the natural tissue with a crosslinking agent. In one preferred embodiment, the cancer/tumor antagonist is ginsenoside Rh2.

Figure 13:
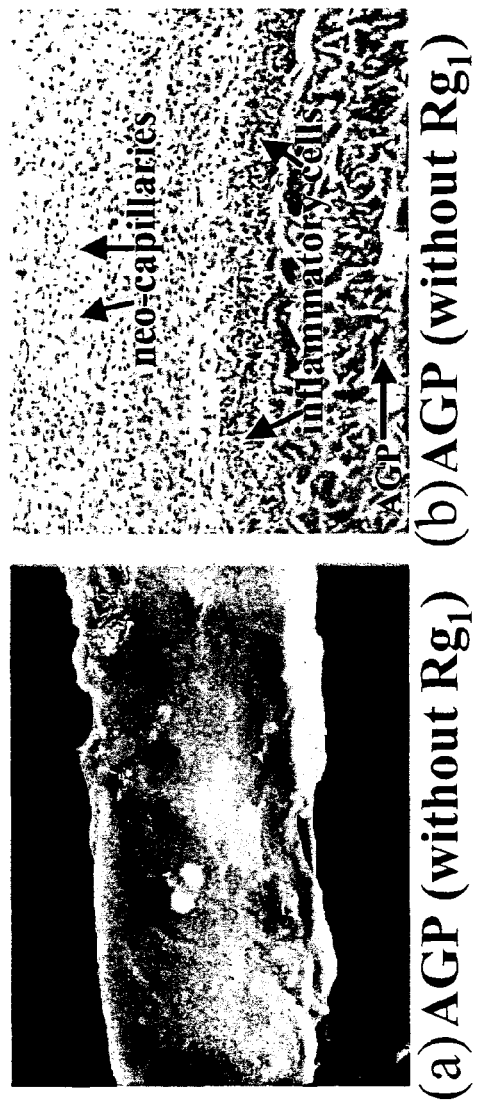
FIG. 13 are cells infiltration extents of genipin-crosslinked acellular bovine pericardia tissue with angiogenesis factors for (a) specimen-AGP, without $Rg_1$; (b) light microscopy of specimen a; (c) specimen-AGP, with $Rg_1$; and (d) light microscopy of specimen c; all explants retrieved at 1-week postoperatively.
Figure 13:
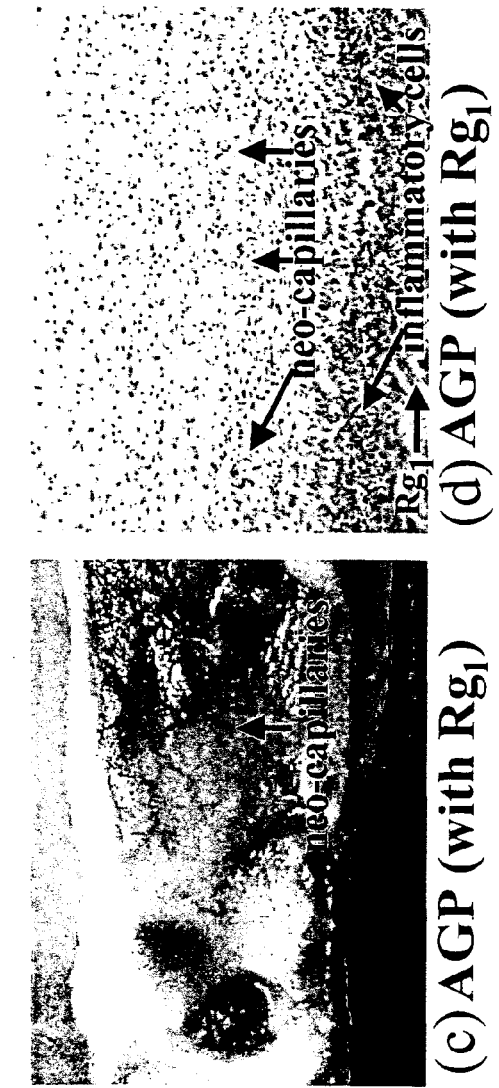

FIG. 13 are cells infiltration extents of genipin-crosslinked acellular bovine pericardia tissue with angiogenesis factors for (a) specimen-AGP, without $Rg_1$; (b) light microscopy of specimen a (specimen-AGP, without $Rg_1$); (c) specimen-AGP, with $Rg_1$; and (d) light microscopy of specimen c (specimen-AGP, with $Rg_1$); wherein all implants are retrieved at 1-week postoperatively. The micro-vessel numbers per field (on a reference basis) are measured under a microscope using an imaging processing software. The micro-vessel density for the $Rg_1$ loaded explant (specimen (b) in FIG. 13) is 778 vessels/$mm^2$ that is statistically significantly higher than the micro-vessel density for the control explant (specimen (d) in FIG. 13) of 341 vessels/$mm^2$.

In some aspects of the present invention, the acellular tissue structure with a porosity increase of more than 5% is also suitable for use in anti-adhesion patches for abdominal surgery, anti-adhesion patches for cardiovascular surgery, acellular matrix for regeneration of myocardiocytes, and vascular grafts.

From the foregoing description, it should now be appreciated that a novel and unobvious process for promoting autogenous ingrowth of damaged or diseased tissue selected from a group consisting of ligaments, tendons, muscle and cartilage has been disclosed for tissue engineering applications. The process comprises a step of surgically repairing the damaged or diseased tissue by attachment of a tissue graft, wherein the tissue graft is formed from a segment of connective tissue protein, the segment being crosslinked with genipin, its analog or derivatives process for providing an acellular shaped or unshaped biomedical material characterized with reduced antigenicity, reduced immunogenicity, and reduced enzymatic degradation. While the invention has been described with reference to a specific embodiment, the description is illustrative of the invention and is not to be construed as limiting the invention. Various modifications and applications may occur to those who are skilled in the art, without departing from the true spirit and scope of the invention.

What is claimed is:

1. A method for promoting autogenous ingrowth of a biological tissue, comprising: providing a natural tissue; removing cellular material from the natural tissue; increasing porosity of said natural tissue by at least 5%; and crosslinking said natural tissue with genipin, said biological tissue being characterized by reduced antigenicity, reduced immunogenicity and reduced enzymatic degradation upon placement inside a patient's body, wherein the step of increasing porosity of the natural tissue is provided by a process selected from a group consisting of an acid treatment process, a base treatment process, and an enzyme treatment process.

2. The method of claim 1 further comprising a step of loading an angiogenesis agent prior to the placement of the biological tissue inside the patient's body.

3. The method of claim 2, wherein the angiogenesis agent is ginsenoside.

4. The method of claim 2, wherein the angiogenesis agent is a growth factor selected from the group consisting of Vascular Endothelial Growth Factor (VEGF), Vascular Endothelial Growth Factor 2 (VEGF 2), basic Fibroblast Growth Factor (bFGF), Vascular Endothelial Growth Factor 121 (VEGF 121), Vascular Endothelial Growth Factor 165 (VEGF 165), Vascular Endothelial Growth Factor 189 (VEGF 189), Vascular Endothelial Growth Factor 206 (VEGF 206), Platelet Derived Growth Factor (PDGF), Platelet Derived Angiogenesis Factor (PDAF), Transforming Growth Factor-β (TGF-β), Platelet Derived Epidermal Growth Factor (PDEGF), Platelet Derived Wound Healing Formula (PDWHF) and combination thereof.

5. The method of claim 1 further comprising a step of loading autologous cells prior to the placement of the biological tissue inside the patient's body.

6. The method of claim 5 further comprises a step of in vitro incubation for a period of time after the step of loading autologous cells.

7. A biological tissue configured and adapted for tissue regeneration, said tissue being characterized by reduced antigenicity reduced immunogenicity and reduced enzymatic degradation upon placement inside a patient's bode with porosity being increased by at least 5%, further comprising an angiogenesis agent or autologous cells.

8. The biological tissue of claim 7, wherein said tissue is selected from a group consisting of a tissue valve, a tissue valve leaflet, a vascular graft, a ureter, a urinary bladder, and a dermal graft.

9. The biological tissue of claim 7, wherein said tissue is selected from a group consisting of a porcine valve, a bovine jugular vein, a bovine pericardium, an equine pericardium, a porcine pericardium, and submucosal tissue.

10. The biological tissue of claim 7, wherein the step of increasing porosity of the tissue is provided by an enzyme treatment process.

11. The biological tissue of claim 7, wherein the step of increasing porosity of the tissue is provided by an acid treatment process.

12. The biological tissue of claim 7, wherein the step of increasing porosity of the tissue is provided by a base treatment process.

13. The biological tissue of claim 7, wherein the angiogenesis agent is ginsenoside.

14. The biological tissue of claim 7, wherein the angiogenesis agent is ginsenoside $RG_1$.

15. The biological tissue of claim 7, wherein the angiogenesis agent is a growth factor selected from the group consisting of Vascular Endothelial Growth Factor (VEGF), Vascular Endothelial Growth Factor 2 (VEGF 2), basic Fibroblast Growth Factor (bFGF), Vascular Endothelial Growth Factor 121 (VEGF 121), Vascular Endothelial Growth Factor 165 (VEGF 165), Vascular Endothelial Growth Factor 189 (VEGF 189), Vascular Endothelial Growth Factor 206 (VEGF 206), Platelet Derived Growth Factor (PDGF), Platelet Derived Angiogenesis Factor (PDAF), Transforming Growth Factor-y (TGF-β), Platelet Derived Epidermal Growth Factor (PDEGF), Platelet Derived Wound Healing Formula (PDWHF) and combination thereof.

16. The method of claim 1, wherein said natural tissue is selected from a group consisting of a tissue valve, a tissue valve leaflet, a vascular graft, a ureter, a urinary bladder, and a dermal graft.

17. The method of claim 1, wherein said natural tissue is selected from a group consisting of a porcine valve, a bovine jugular vein, a bovine pericardium, an equine pericardium, a porcine pericardium, and submucosal tissue.

18. The method of claim 2, wherein the angiogenesis agent is ginsenoside $RG_1$.

* * * * *